United States Patent
Berger et al.

(10) Patent No.: US 7,720,696 B1
(45) Date of Patent: May 18, 2010

(54) COMPUTERIZED SYSTEM FOR TRACKING HEALTH CONDITIONS OF USERS

(75) Inventors: Mark Berger, Houston, TX (US); Helen Francis Berger, Houston, TX (US)

(73) Assignee: MK3SD, Ltd, Houston, TX (US)

( * ) Notice: Subject to any disclaimer, the term of this patent is extended or adjusted under 35 U.S.C. 154(b) by 199 days.

(21) Appl. No.: 11/679,029

(22) Filed: Feb. 26, 2007

(51) Int. Cl.
*G06Q 10/00* (2006.01)

(52) U.S. Cl. .................. 705/3; 705/2; 705/4; 600/300; 600/301

(58) Field of Classification Search ................. 705/2–4; 600/300–301
See application file for complete search history.

(56) References Cited

U.S. PATENT DOCUMENTS

| | | | | |
|---|---|---|---|---|
| 6,083,173 A * | 7/2000 | Grant et al. | ................. | 600/529 |
| 6,112,181 A * | 8/2000 | Shear et al. | ..................... | 705/1 |
| 6,368,287 B1 * | 4/2002 | Hadas | ........................ | 600/529 |
| 7,309,314 B2 * | 12/2007 | Grant et al. | ................. | 600/529 |
| 2002/0143578 A1 * | 10/2002 | Cole et al. | ...................... | 705/2 |
| 2003/0177389 A1 * | 9/2003 | Albert et al. | ................ | 713/201 |
| 2005/0159986 A1 * | 7/2005 | Breeland et al. | ............... | 705/3 |
| 2007/0214013 A1 * | 9/2007 | Silverman | ...................... | 705/2 |
| 2008/0146893 A1 * | 6/2008 | Levendowski et al. | ...... | 600/300 |

* cited by examiner

*Primary Examiner*—Vivek D Koppikar
(74) *Attorney, Agent, or Firm*—Buskop Law Group, PC; Wendy Buskop

(57) ABSTRACT

A computerized system of tracking health conditions of users associated with a client for diagnosing sleep apnea through forming an encrypted web based questionnaire. The user inputs information such as company personal information, individual personal information, health information, and personal health information. This information is then electronically compiled and a health screening service report is outputted such as witnessed sleep apnea, self admitted sleep apnea, body mass index of each user, and summary of results of a sleep test.

12 Claims, 11 Drawing Sheets

Health Screening Survey
Step 1 of 3

Company Information
Company: [_____100_____]   Driver #: [__102__]
Classification: [__104__]   Location: [__106__]
Date of Hire: [____] ☐ ☐ YES, I am an applicant!
                108

Personal Information
Last Name: [__110__]   First Name: [__112__]   MI: [114]
DOB: [____116____]   SSN: [_____]
                                            118
Sex: [__]   Height: [__]   Weight: [__] (lbs.)
120            122              124

[Continue to Step 2]

FIG. 2

Health screening survey
Step 2 of 3
For each question below, please choose the response that best fits your answer for that Question.

| Health information Question | Answers | |
|---|---|---|
| 1. Do you have high blood pressure? | ⊙ Yes ⊙ No | ⌐ 134 |
| 2. Do you have diabetes? | ⊙ Yes ⊙ No | ⌐ 136 |
| 3. Have you been treated for heartburn? | ⊙ Yes ⊙ No | ⌐ 138 |
| 4. Do you have heart problems? | ⊙ Yes ⊙ No | ⌐ 140 |
| 5. Have you ever undergone a heart operation or procedure? | ⊙ Yes ⊙ No | ⌐ 142 |
| 6. Do you take any of the following medications: isorbide dinitrate, Isordil, Ismo, nitroglycerin, amiadarone or Cardarone? | ⊙ Yes ⊙ No | ⌐ 144 |
| 7. Do you have sleep apnea? | ⊙ Yes ⊙ No | ⌐ 146 |
| 8. Do you take any of the following medications: Glucophage, Glucotrol, Actos or Avandia, or any other diabetes medications? | ⊙ Yes ⊙ No | ⌐ 148 |
| 9. Do you have COPD (emphysema)? | ⊙ Yes ⊙ No | ⌐ 150 |
| 10. Do you have asthma? | ⊙ Yes ⊙ No | ⌐ 152 |
| 11. Have you been treated for depression? | ⊙ Yes ⊙ No | ⌐ 154 |
| 12. Do you snore louder than talking? | ⊙ Yes ⊙ No | ⌐ 156 |
| 13. Does your snoring bother other people? | ⊙ Yes ⊙ No | ⌐ 158 |
| 14. Do you take any of the following medications: Plavix, Trental, or Persantine? | ⊙ Yes ⊙ No | ⌐ 160 |
| 15. Do you take ANY of the following medications: Protonix, Prevacid, Nexium, Pepcid, or Tagamet? | ⊙ Yes ⊙ No | ⌐ 162 |
| 16. On average, do you urinate more than once per night? | ⊙ Yes ⊙ No | ⌐ 164 |
| 17. Do you become drowsy while driving? | ⊙ Yes ⊙ No | ⌐ 166 |
| 18. Does head, back, neck, or joint pain affect your sleeping? | ⊙ Yes ⊙ No | ⌐ 168 |
| 19. Do you take any of the following medications: Vasotec, Cozar, Lotril, Norvasc, Enalapril, Lisinopril, Hydrolchlothiazide, or Lasix? | ⊙ Yes ⊙ No | ⌐ 169 |
| 20. Do you take any of the following medications: Inderal, Toprol, Metoprolol, Coreg, or Lopressor? | ⊙ Yes ⊙ No | ⌐ 170 |
| 21. Do you take any of the following medications: Digoxin, or Coumadin? | ⊙ Yes ⊙ No | ⌐ 172 |
| 22. Do you sleep restlessly or find the blankets on the floor in the morning? | ⊙ Yes ⊙ No | ⌐ 174 |
| 23. Has anyone noticed that you quit breathing during your sleep? | ⊙ Yes ⊙ No | ⌐ 176 |
| 24. Have you awakened from sleep with gasping breaths? | ⊙ Yes ⊙ No | ⌐ 178 |

Continue to Step 3

FIG. 3

Health Screening Survey
*Step 3 of 3*
Situational Information
Please indicate your chance of dozing under each of the following scenerios

| Situation | Chance of Dozing | | |
|---|---|---|---|
| | | | |
| 1. Sitting and reading | ⊙ Never ⊙ Slight | ⊙ Moderate | ⊙ High — 180 |
| 2. Watching TV | ⊙ Never ⊙ Slight | ⊙ Moderate | ⊙ High — 182 |
| 3. Sitting inactive in a public place (e.g., a theater or meeting) | ⊙ Never ⊙ Slight | ⊙ Moderate | ⊙ High — 184 |
| 4. As a passenger in a car for an hour without a break | ⊙ Never ⊙ Slight | ⊙ Moderate | ⊙ High — 186 |
| 5. Lying down to rest anytime circumstances permit | ⊙ Never ⊙ Slight | ⊙ Moderate | ⊙ High — 188 |
| 6. Sitting and talking to someone | ⊙ Never ⊙ Slight | ⊙ Moderate | ⊙ High — 190 |
| 7. Sitting quietly after lunch without alcohol | ⊙ Never ⊙ Slight | ⊙ Moderate | ⊙ High — 192 |
| 8. In a truck or car, while stopping for a few minutes in traffic | ⊙ Never ⊙ Slight | ⊙ Moderate | ⊙ High — 194 |

For Men Only!
What is your neck size? ☐ — 195

[ Submit Survey ]

FIG. 4

Health Screening Survey — 196

Thank you, USER NAME!
We appreciate your taking the time to complete this health screening survey. Your information has been securely processed, and as with all personal medical records, will be kept confidential.

*FIG. 5*

Example Company Health Screening Survey Rankings

You currently have a total of 86 survey respondents, which have been broken down into six categories based on sex, WA (Witnessed Apnea), and EDS (Excessive Daytime Sleepiness).

Respondents —198

| Sex | WA+ | EDS+ / WA- | EDS- / WA- |
|---|---|---|---|
| Male | 26 | 5 | 44 |
| Female | 2 | 1 | 8 |

—199  —200

Find a Survey

SSN: [ ][ ][ ]  Find —206
Driver #: [ ]  Find —208
Last Name: [ ]  Find —210

There are currently 14 respondents that have been marked for immediate contact due to self-admitted Sleep Apnea. To view a complete list, click here.

To review survey respondents based on more specific criteria, click here for additional reporting tools.

[ Return to Main Menu ]

*FIG. 6*

Example Company Survey Respondents: Sleep Apnea Alert!

| | Name | SSN | Location | Driver No. | Sex | WA± | Probability | Alert | Date | Date of Hire | Status |
|---|---|---|---|---|---|---|---|---|---|---|---|
| 1. | Berger, Mark B | 123-45-6711 | Location A | 007 | Male | ⊕ | 1.000 | 🔔 | 3/27/2006 | 3/27/2005 | |
| 2. | berger, mark b | 222-22-222 | Location B | 123 | Male | ⊕ | 1.000 | 🔔 | 2/13/2007 | 2/13/2005 | |
| 3. | Green, Paul | 123-45-6711 | Location B | 00000 | Male | ⊕ | 1.000 | 🔔 | 2/15/2006 | 2/15/2005 | |
| 4. | Michael, Johnson | 999-8897766 | Location A | 000066 | Male | ⊖ | 1.000 | 🔔 | 11/15/2006 | 11/15/2005 | |
| 5. | Smith, James | 123-45-6776 | Location A | abc123 | Male | ⊕ | 1.000 | 🔔 | 11/22/2006 | 11/22/2005 | |
| 6. | Test, Test T. | 111-11-1111 | Location A | 111111 | Male | ⊖ | 1.000 | 🔔 | 2/16/2007 | 2/16/2005 | |
| 7. | O'Grady, John | 123-45-6711 | Location B | 00000 | Male | ⊖ | 0.594 | 🔔 | 2/15/2006 | 2/15/2005 | ✉ |
| 8. | Gordon, John | | Location A | 00000 | Male | ⊕ | 1.000 | 🔔 | 2/15/2006 | 2/15/2005 | |
| 9. | Fills, Christopher | | Location B | 00000 | Male | ⊕ | 0.666 | 🔔 | 2/15/2006 | 2/15/2005 | |
| 10. | Turk, Larry | | Location B | 00000 | Male | ⊕ | 0.985 | 🔔 | 2/15/2006 | 2/15/2005 | ✉ ⊙ |
| 11. | Brady, Kim | | Location B | 00000 | Female | ⊖ | 0.000 | 🔔 | 2/15/2006 | 2/15/2005 | ✉ ⊙ |

Download Report

*FIG. 7*

Health Screening Survey Results: *Berger, Mark B.*

Personal Information

| | | |
|---|---|---|
| 232 — Name | Berger, Mark B. | [Change] — 249 |
| 234 — SSN | 123-45-7-6711 | |
| | Company: | Example Company |
| | Classification: | N/A |
| 236 — Location | Location A | [Change] — 249 |
| 238 — Driver # | 007 | [Change] — 249 |
| | Applicant: | No | [Change] — 249 |
| 240 — Sex | Male | [Change] — 249 |
| | Age: | 51 yrs. (DOB 4/15/1956) |
| | Height: | 5' 11" |
| | Weight: | 213 (lbs.) |

[Comments] (Edit) — 251

[Delete Survey]

Scoring — 246

Probability Score: 1.000
WA ⊕   EDS ⊕   BMI: 29.7 — 245
                    244

248 —

*This user has been flagged for a Sleep Apnea Follow-up call!*

[Remove Apnea Flag]

Sleep Test
This individual has no available test results.

Follow Up
There has been no follow-up with this individual.

[Modify]

*FIG. 8A*

Complete List of Survey Responses (Recorded on 3/27/2006)

Health Information

1. Do you have high blood pressure? — Yes
2. Do you have diabetes? — Yes
3. Have you been treated for heartburn? — Yes
4. Do you have heart problems? — No
5. Have you ever undergone a heart operation or procedure? — No
6. Do you take ANY of the following medications: Isordil, Ismo, nitroglycerin, Cardarone, or Amiodarone? — No
7. Do you have sleep apnea? — Yes
8. Do you take ANY of the following medications: Glucophage, Glucotrol, Actos, or Avandia, or any other diabetes medications? — Yes
9. Do you have COPD (emphysema)? — No
10. Do you have asthma? — No
11. Have you been treated for depression? — No
12. Do you snore louder than talking? — Yes
13. Does your snoring bother other people? — No
14. Do you take ANY of the following medications: Plavix, Trental, or Persantine? — No

Epworth Information

1. Sitting and reading — Never
2. Watching TV — Never
3. Sitting inactive in a public place (e.g., a theater or meeting) — Never
4. As a passenger in a car for an hour without a break — High
5. Lying down to rest anytime circumstances permit — Moderate
6. Sitting and talking to someone — Slight
7. Sitting quietly after lunch without alcohol — Never
8. In a truck or car, while stopping for a few minutes in traffic — Never

Sex-Specific Information

What is your neck size?

*FIG. 8B*

Complete List of Survey Responses (Recorded on 3/27/2006)
Health Information

15. Do you take ANY of the following medications: Protonix, Prevacid, Nexium, Pepcid, or Tagamet? — No
16. On average, do you urinate more than once per night? — No
17. Do you become drowsy while driving? — Sometimes
18. Does head, back, neck, or joint pain affect your sleeping? — Yes
19. Do you take ANY of the following medications: Vasotec, Cozar, Lotril, Norvasc, Enalapril, Lisinopril, Hydrochlorthiazide, or Lasix? — Yes
20. Do you take ANY of the following medications: Inderal, Toprol, Metoprolol, Coreg, Lopressor? — No
21. Do you take ANY of the following medications: Digoxin, Coumadin? — Yes
22. Do you sleep restlessly or find the blankets on the floor in the morning? — Yes
23. Has anyone noticed that you quit breathing during your sleep? — No
24. Have you awakened from sleep with gasping breaths? — Yes

Screening History

| | Date | BMI | WA± | Probability | Alert | Status |
|---|---|---|---|---|---|---|
| 1. | 3/27/2006 | 29.7 | ⊕ | 1.000 | 🔔 | |

*FIG. 8C*

Example Company Survey Respondents: Female / EDS- / WA-Filter/Sort Options

252 — Classification: <All Classifications> ▼   Location: <All Locations> ▼   Treatment Facility: <All Facilities> ▼   256

258 — Sort by: Risk ▼ Desc.   Then by: Date of Entry ▼ Desc.

Download Report

Apply Filter

<Previous   Page 1 of 1

26 Result(s) found

| Name | SSN | Location | Driver No. | Sex | WA± | Probability | Alert | Date | Date of Hire | Status |
|---|---|---|---|---|---|---|---|---|---|---|
| 1. Barna, John | | Location A | 00000 | Male | ⊕ | 1.000 | | 3/27/2006 | 3/27/2005 | |
| 2. Berger, Mark B | 123-45-6711 | Location A | 007 | Male | ⊕ | 1.000 | 📜 | 3/27/2006 | 3/27/2005 | |
| 3. berger, mark b | 222-22-222 | Location B | 123 | Male | ⊕ | 1.000 | 📜 | 2/13/2007 | 2/13/2005 | |
| 4. Elk, Christopher | | Location A | 00000 | Male | ⊕ | 1.000 | | 2/15/2006 | 2/15/2005 | |
| 5. Green, Paul | | Location B | 00000 | Male | ⊕ | 1.000 | 📜 | 11/15/2006 | 11/15/2005 | |
| 6. Lincoln, Larry | 666-55-4444 | Location A | 00000 | Male | ⊕ | 1.000 | | 11/22/2006 | 11/22/2005 | |

*FIG. 9*

COMPUTERIZED SYSTEM FOR TRACKING HEALTH CONDITIONS OF USERS

FIELD

The present embodiments relate generally to a computerized system of tracking health conditions of users associated with a client for screening for sleep apnea.

BACKGROUND

Sleep apnea is very common, particularly in the commercial driver population. Studies show that up to 28% of commercial drivers may be afflicted. Primary risk factors include being male, overweight, and over the age of forty. Fortunately, sleep apnea can be diagnosed and, with treatment, quality of life and health benefits can be realized.

There exists a need for a computerized system to accurately screen for sleep apnea among commercial drivers.

Sleep apnea is defined as the cessation of breathing during sleep. Obstructive sleep apnea (OSA) is the most common form of sleep apnea. OSA occurs when the tissues in the back of the throat repetitively collapse during sleep, producing snoring and complete airway blockage. This blockage creates pauses in breathing that occur repeatedly every night. In severe cases, these blockages can occur as frequently as every 30 seconds. Alarmingly, they can last up to a full minute.

There exists a need for a computerized system in which screening for sleep apnea in large populations can be automated on an ongoing basis.

Repetitive pauses in breathing during sleep are accompanied by a reduction in blood oxygen levels and are followed by an arousal response. This response includes a release of substances into the bloodstream, which promote elevation of blood pressure, inflammation, insulin resistance, and a disruption of the brain wave sleep pattern. The consequences of untreated sleep apnea include poor quality sleep, excessive daytime fatigue and sleepiness, an increased risk for vehicular accidents, irritability, hard-to-control high blood pressure and diabetes, heart disease, and stroke. Interestingly and not coincidentally, many of these same medical conditions account for the majority of health-related expenditures in the commercial driver population. Moreover, untreated sleep apnea may be responsible for job impairment and motor vehicle crashes.

There exists a need for a computerized system to monitor those associated with risks of sleep apnea.

There exists a need for a computerized system to determine whether an individual is at high risk for sleep apnea.

There exists a need for a computerized system to provide administrative functions for a sleep apnea program.

The present embodiments meet these needs.

BRIEF DESCRIPTION OF THE DRAWINGS

The detailed description will be better understood in conjunction with the accompanying drawings as follows:

FIG. 2 shows an example health screening survey requesting company personal information and individual personal information.

FIG. 3 shows an example health screening survey requesting health information.

FIG. 4 shows an example health screening survey requesting situational answers from a situational questionnaire.

FIG. 5 shows an example of a thank you screen that is shown after completing the health screening survey.

FIG. 6 shows an example screen of survey rankings of how an administrator would view users after they had completed the health screening survey.

FIG. 7 shows an example survey rankings.

FIG. 8 shows a screen of an user after an administrator had selected them and their answers to the health screening questions.

FIG. 9 shows the ability of an administrator to filter between different users that are in the database.

Figure 1:
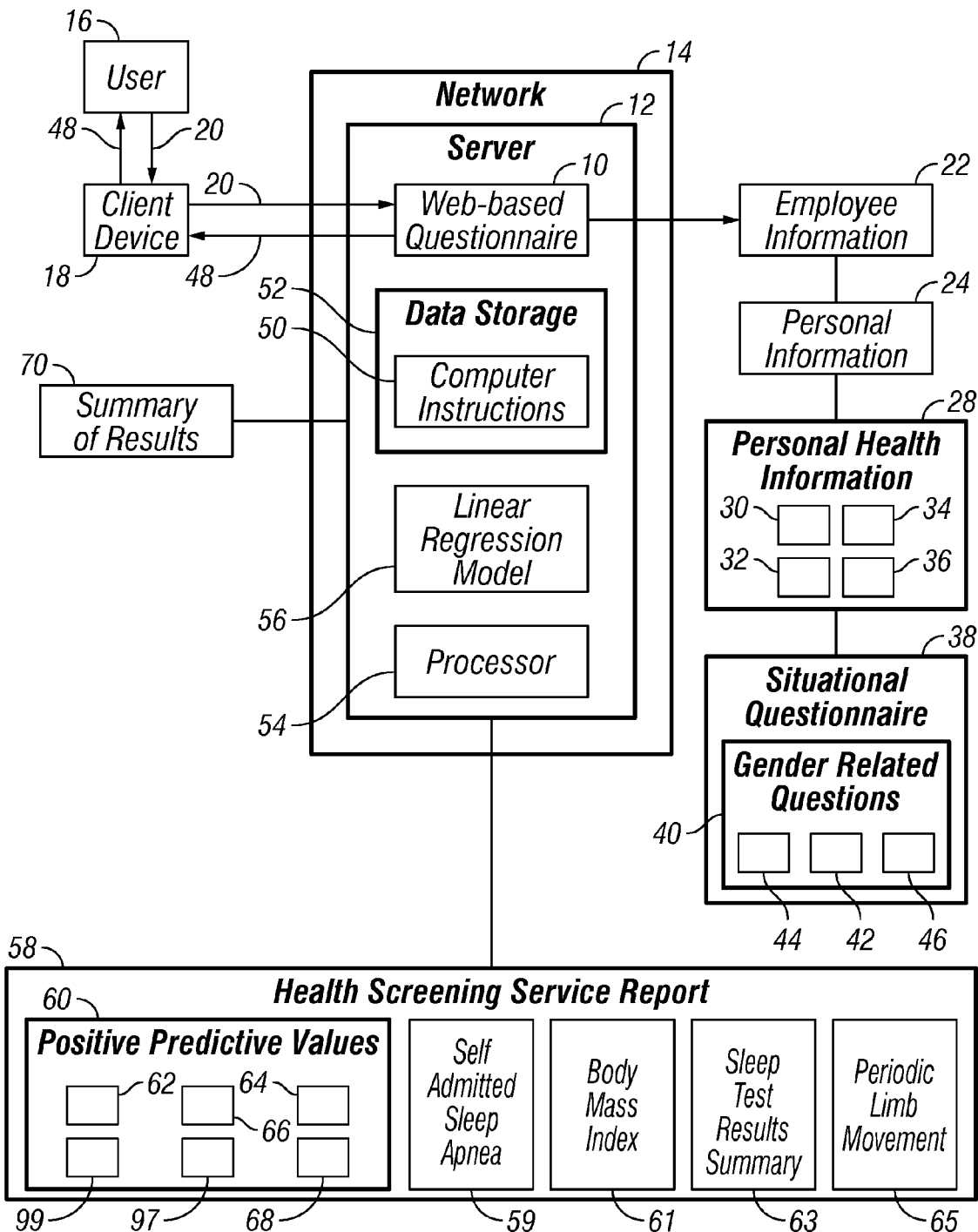
FIG. 1 depicts a diagram of how an embodiment of the computerized system operates.

The present embodiments are detailed below with reference to the listed Figures.

DETAILED DESCRIPTION OF THE EMBODIMENTS

Before explaining the present embodiments in detail, it is to be understood that the embodiments are not limited to the particular embodiments and that they can be practiced or carried out in various ways.

The present embodiments relate to a computerized system for tracking health conditions of users associated with a client for screening for sleep apnea risk. A client could be an insurance company, a risk management company, a trucking company, a commercial carrier, a government agency, a military organization, or any other type of company, corporation, partnership, or other organization.

The computerized system supplies an encrypted web based questionnaire resident on a server, accessible through to obtain input information concerning risk of sleep apnea for at least one user, with or without the user being aware the questionnaire is for determining sleep apnea. The user can input information regarding sleep apnea such as company employee information, individual personal information, personal health information, and response to situational questionnaires.

Company employee information can include information such as company name, date of hire, operating center location, whether the user is an applicant or an existing employee and the employee number or driver number of the user, such as a driver license number, a social security number, or another number to identify the user.

Individual personal information can include information such as the name of an user, gender of the user, social security number of the user, the age of an user, weight of an user, height of a user, date of birth of an user, an employee number or driver number of an user, the date of hire of the user, and the date of input of information. Other individual personal information can be included as designated by a client.

Personal health information can include user reported high blood pressure or hypertension, user reported diabetes, user reported heart conditions, self-admitted sleep apnea, user reported emphysema or lung disease, user reported asthma, and user reported depression. Personal health information concerning physical symptoms can also be used, such as snoring, user reported heart burn, user reported frequent urination at night, witnessed sleep apnea, excessive daytime sleepiness, restless sleeping, awakening at night with gasping breaths, and drowsiness while driving. Additional personal information concerning prior operations can be used, such as prior heart operations. Additionally, medications that the user is currently taking can be used, such as antihypertensive medicine, oral hypoglycemic medicine, cardiac medications, anticoagulants, antacids or proton pump inhibitors.

One or more situational questionnaires can also be provided. The situational questionnaires can include information relevant to the Epworth sleep scale. The Epworth sleep scale can be obtained using situational questions, such as responding with a chance of dozing during a variety of situations, ranging from never, slight, moderate, to high. These situations can include sitting and reading, watching TV, sitting inactive in a public place (e.g., a theatre or meeting), as a passenger in a car for an hour without a break, lying down to rest anytime circumstances permit, sitting and talking to someone, sitting quietly after lunch without alcohol, in a truck or car while stopping for a few minutes in traffic. In addition gender specific questions such as, neck size for male users and menopausal questions for female users can also be included.

Acknowledgement that the encrypted web based questionnaire is complete can be provided to the user from the server. Acknowledgement can include a specific screen indicating the completion of the questionnaire and thanking the user. Acknowledgement can also include an e-mail sent to the user, which can include a copy of the user's responses to the questionnaire. An individualized web based health screening service report can be provided to the user after completion of the encrypted web based questionnaire. The individualized health screening report can be provided as part of the acknowledgement, or separately.

The information that is inputted is categorized using computer instructions in the server for instructing a processor in the server to categorize the user into one of six categories based on the input information, each category requiring a form of statistical analysis. The categories are: male Witnessed Apnea Positive(WA+), female Witnessed Apnea Positive(WA+), male Excessive Daytime Sleepiness Positive (EDS+) with negative witnessed apnea(WA−) requiring an odds ratio calculation in combination with a linear regression model, female Excessive Daytime Sleepiness Positive (EDS+) with negative witnessed apnea(WA−) requiring an odds ratio calculation, male Witnessed Apnea Negative (WA−) and Excessive Daytime Sleepiness Negative(EDS−) requiring an odds ratio calculation, and female Witnessed Apnea Negative(WA−) and Excessive Daytime Sleepiness Negative(EDS−) requiring an odds ratio calculation.

The computerized system can additionally provide a web based health screening service report using the categorized input information that includes at least one rating per each user. The rating can include individualized numerical scores indicating a positive predictive value, a rating of "high," "medium," or "low" positive predictive value for the user, or combinations thereof. The web based health screening service report can have different sections. Some of the different sections can include a summary of all positive predictive values section, a self admitted sleep apnea section, a body mass index section, a summary section of results of a sleep test, and a section of periodic limb movements recorded during a sleep test.

The positive predictive values can be indicated by a red, yellow, or green flag indicating high, intermediate, or low risk for sleep apnea, respectively. It is contemplated that colors alone can be used without any specific icon to indicate high, medium, or low positive predictive values. It is also contemplated that textual words, high, medium, and low can be used in association with commercial drivers to indicate high, medium, or low positive predictive values.

In the summary of all positive predictive values section, the different categories for the categorized input information can be listed. In the body mass index section, an user's body mass index can be calculated and shown. The body mass index is a ratio of an user's weight and height displayed in numerical form. In the summary section of results of a sleep test, different information can be provided such as an apnea/hypopnea index, the number of times per hour a cessation or near cessation in breathing occurs for a user, an oxygen saturation nadir for a user, the lowest saturation of blood oxygen reported during the sleep test, and an oxygen desaturation index, the number of times per hour oxygen saturation drops by at least 4% for the user. In the periodic limb movements recorded during a sleep test section, presence of stereotypical limb movements associated with EEG arousal during a sleep test are recorded and analyzed.

It is contemplated that the method can also include directing a user to a physician to prescribe a sleep test for sleep apnea, and obtain the results of the sleep test.

In one embodiment of the invention, a sleep apnea diagnostic screening questionnaire report for the client can comprise information such as a user's name, a client's name, the sex of the user, self-admitted sleep apnea, user height, user weight, user reported hypertension, user reported diabetes, user reported heat disease, neck size range of the user, user reported lung disease, user reported asthma, user reported heart burn, user reported frequent urination, and combinations thereof.

In an alternate embodiment the summary results of the sleep test can be linked to an electronic copy of the complete results of the sleep test, such as a report including stages of sleep, time of sleep, number of respiratory events per hour of sleep, number of oxygen desaturations per hour of sleep, presence or absence of limb movements during sleep, and other findings of a sleep test.

In one embodiment the summary of all positive predictive values can include witnessed sleep apnea WA+ or WA−, probability value for sleep apnea, in addition to administrative status and data selected from information such as the name of a user, the name of a client, an employee number for each user, the gender for each user, the social security number for each user, an alert icon for self admitted sleep apnea, date of input of information, date of hire of the user, at least one client designated field, and combinations thereof. The summary of all positive predictive values can be categorized by administrative status, company employee information, individual personal information, personal health information, answers to the situational questionnaire, and combinations thereof.

In an alternate embodiment users with self admitted sleep apnea can be flagged for additional validation data support self-admitted sleep apnea.

In one embodiment the web based health screening service report can enable a client to look up a particular user by name, employee number or a social security number. It is contemplated that the health screening service report can include a look-up table, such as a search field for entering information, for locating users by name, employee number, social security number, or other information.

In one embodiment computer instructions can include a dataset generated using outcomes from over 500 users, forming a linear regression model. An odds ratio model was first utilized in determining risk stratification for sleep apnea in all groups. Individual odds ratios were assigned to specific health conditions and specific symptoms based on results from published medical research. These odds ratios were modified based on outcome data available on 115 commercial drivers tested for sleep apnea. A composite odds ratio value was calculated as the product of all individual odds ratios. Retrospective analysis of 115 commercial drivers tested for sleep apnea demonstrated that a composite odds ratio of 8.0 or greater for male, and 1.9 or greater for female, Witnessed Apnea Negative (WA−) and Excessive Daytime Sleepiness Negative (EDS−) would generate a high positive predictive value of at least 85%. A subsequent analysis of an additional over 500 commercial drivers tested for sleep apnea confirmed an 88% positive predictive value for these groups from this odds ratio model.

A retrospective analysis of 115 commercial drivers tested for sleep apnea demonstrated that the presence of witnessed apnea (WA+) was highly predictive for sleep apnea. For this reason, all commercial drivers reporting witnessed apnea were considered at high risk for sleep apnea. A subsequent analysis of an additional over 500 commercial drivers tested for sleep apnea confirmed a 90% positive predictive value for this single risk factor.

Subsequent analysis of an additional over 500 commercial drivers confirmed the aforementioned statistical model capable of a greater than 85% positive predictive value for sleep apnea in all groups except for male Excessive Daytime Sleepiness Positive (+), Witnessed Apnea (−). For this group it was necessary to apply a linear regression following a composite odds ratio calculation.

To generate the linear regression model for all male users indicating a positive response for excessive daytime sleepiness EDS (+), witnessed apnea negative WA (−), was created by exploring all possible models with main effects and pairwise interactions with the following variables: body mass index, age, hypertension, diabetes, heartburn, heart condition, snoring, asthma, depression, frequent urination at night, and painful sleep.

The "best" model was chosen by using both forward and backward selection using the aic criterion (the function step in R). After selecting this model, subjects were assigned a probability of apnea (inverse log odds of linear combination). Using the usual 0.5 cutoff on the estimated probability, a cross-validated positive-predictive value of 0.876 was achieved. To get to the goal of 0.88, a cutoff of 0.65 was preferred. This gave an estimated 0.891 positive predictive value using cross-validation.

In one embodiment the users are drivers, and the clients are commercial carriers. It is contemplated that any body of users could be screened using the present embodiments, such as chemical and petrochemical plant employees, bus drivers, truck drivers, cab drivers, boat pilots, railroad engineers, railroad conductors, boat captains, military personnel, law enforcement personnel, emergency response personnel, medical professionals, drillers, miners, or operators of heavy machinery. In an embodiment, the users can be subscribers or covered individuals of a health insurance policy. In another embodiment, the users can be employees of clients of risk management companies.

A male commercial truck driver is provided access to the computerized system, such as through a client interne site. The male commercial truck driver can input requested information into the computerized system using one or more screens, questionnaires, or surveys. Alternatively, a male commercial truck driver can provide requested information in another form, such as a handwritten response to one or more questionnaires or surveys, and the requested information can be input into the computerized system by a third party.

Specifically, a male commercial truck driver can be asked to input his neck size, which is relevant in screening for sleep apnea.

The computerized system then processes the information inputted by the male commercial truck driver according to the linear regression model or odds ratio calculation utilized by the computerized system. The computerized system then provides a probability value indicating a likelihood or lack thereof of sleep apnea.

A female commercial truck driver is similarly provided access to the computerized system and can similarly input requested information into the computerized system or can provide requested information in the form of a handwritten response. Specifically, a female commercial truck driver can be asked questions regarding menopausal status or estrogen replacement therapy. The computerized system then similarly processes the information to provide a probability value indicating a likelihood or lack thereof of sleep apnea.

In an alternate embodiment menopausal questions can include whether a female user is premenopausal, whether a female user is post menopausal, or whether a female user uses estrogen replacement therapy.

In one embodiment all elements of the web based questionnaire must be completed before a user is permitted to progress to the next screen.

In one embodiment the web based questionnaire is HIPAA compliant based on the United States Health Insurance Portability and Accountability Act (HIPAA) of 1996, the final regulation of the HIPAA privacy rule of December 2000, and the Final Rule modifications of August 2002. It is contemplated that each user can supply a HIPAA compliant release under the United States Health Insurance Portability and Accountability Act of 2002, 42 C.F.R. §164, and that the present method can include confirming the presence of a HIPAA compliant release for each user. It is further contemplated that any protected health information (PHI) obtained using the present method can be de-identified when stored and processed to further comply with the requirements of HIPAA.

In an alternate embodiment, the user can authenticate one or more documents, such as documents indicating receipt of sleep apnea treatment and compliance information. Documents authenticated by the user can be scanned, entered, or otherwise recorded into the computerized system with the user's sleep apnea information.

In one embodiment additional reports such as compliance reports are included with the user's sleep apnea information.

It is contemplated that results produced can be sorted and filtered by a number of categories, including probability of sleep apnea, administrative status, date of hire, date of entry, and other information. In an embodiment, the input information can include general health information, such as information relating to high blood pressure, diabetes, and other conditions.

In an embodiment, the present computerized system can be linked to other medical databases, from which health information can be retrieved. It is contemplated that user information could be automatically collected and stored in this fashion.

The present computerized system of tracking health conditions of users associated with a client for screening for sleep apnea possesses an extremely high positive predictive value. A high positive predictive value allows a client to streamline otherwise costly, inefficient, and cumbersome procedures by recommending sleep testing only for users who indicate a high likelihood of testing positive for sleep apnea. This benefit can often permit a client that would be unwilling, or financially unable, to dedicate sufficient time and resources to a more cumbersome and expensive series of tests to screen a body of employees for sleep apnea.

The present computerized system is extremely adaptable and can be specifically tailored to meet any client's needs. The present computerized system can also be tailored to screen specific bodies of users, such as commercial truck drivers, chemical or petrochemical plant workers, and other bodies of users.

The present computerized system can be entirely internet-based, using simple interfaces, causing it to be extremely easy and efficient to use, such that any body of users or clients can utilize the present computerized system. The present computerized system also possesses numerous administrative management capabilities, such as allowing user-entered data to be sorted and filtered, and allowing specific users or user-related data to be located using one or more identifiers.

The present computerized system can screen for sleep apnea, preventing potentially dangerous vehicular accidents, thereby preventing costly loss or damage of equipment, and loss of time, preventing injury, and saving lives. Treatment of sleep apnea has also been shown to improve ones health through better control of blood pressure and diabetes, and reduces risk for heart attacks and stroke.

FIG. 1 depicts a diagram of how the computerized system operates. The computerized system tracks health conditions of users associated with a client for diagnosing sleep apnea through supplying an encrypted web based questionnaire (10) resident on a server (12), accessible through a network (14) for completion by at least one user (16). A client device (18), such as a computer, can be used to access network (14). The network (14) can be the interne, or any public or private database. It is contemplated that a network can be a centralized database, fully accessible by an administrator, wherein an individual client can access only information relating to employees of the individual client.

The user provides input information (20) to the encrypted web based questionnaire (10), such as company employee information (22), individual personal information (24), personal health information (28), and responses to a situational questionnaire (38) including gender related questions (40).

Personal health information (28) can include health conditions (30), such as diabetes, hypertension, or heart conditions, personal symptoms (32), prior operations (34), such as heart operations, and medications (36), such as digoxin, or beta blockers.

The situational questionnaire (38) includes gender related questions (40) such as gender indicators (42), neck size for male users (44), and menopausal questions for female users (46), such as "Are you a female over the age of fifty?", or "Are you taking estrogen replacement therapy?"

The computerized system can also include an acknowledgement (48), such as by e-mail, to the user (16) from the server (12) that the encrypted web based questionnaire (10) is complete. The acknowledgement (48) can also include a copy of the user's responses to the encrypted web based questionnaire (10) for the user's records. The acknowledgment (48) can also include an individualized health screening service report to the user (16).

The computerized system can also include categorizing the input information (20) using computer instructions (50) on the server (12). Server (12) is depicted having data storage (52) containing computer instructions (50). Data storage (52) is depicted in communication with a processor (54). Processor (54) can be used to determine a probability, such as by using a linear regression model (56), to determine a rating relating to risk of sleep apnea. Other calculations, such as an odds ratio calculation, can be used in place of linear regression model (56).

The computerized system includes providing a health screening service report (58). The health screening service reports includes a summary of all positive predictive values (60), which can include categories such as male witnessed sleep apnea +(WA+) (62), female witnessed sleep apnea+ (WA+) (64), male witnessed sleep apnea–(WA–) and excessive daytime sleepiness positive (EDS+) (66) female witnessed sleep apnea–(WA–) and excessive daytime sleepiness positive (EDS+) (68), male witnessed sleep apnea–(WA–) and excessive daytime sleepiness–(EDS–) (99), and female witnessed sleep apnea–(WA–) and excessive daytime sleepiness (EDS–) (97).

Health screening service report (58) also has a self admitted sleep apnea section (59), which identifies whether a user has indicated he or she has sleep apnea. Health screening service report (58) further has a body mass index section (61), which calculates and displays a user's body mass index. Health screening service report (58) also as a summary results of sleep test section (63), which can display apnea/hypopnea index for a user, oxygen saturation nadir for the user, and an oxygen desaturation index for the user. Health screening service report (58) additionally has a periodic limb movement section (65), which indicates the presence of stereotypical limb movements associated with EEG arousal during a sleep test.

The computerized system can identify users of the encrypted web based questionnaire having self admitted sleep apnea and direct the user to a physician to prescribe a sleep test. The computerized system can then include providing a summary of results (70) of a sleep test for the user (16). The summary of results (70) of the sleep test for the user has an apnea/hyperpnoea index, an oxygen saturation nadir for a user, an oxygen desaturation index, and a periodic limb movements recorded during the sleep test or combinations thereof.

FIG. 2 shows an example health screening survey requesting company personal information and individual personal information. Company information that a user may input include name of Company (100), such as Precision Pulmonary Diagnostics, Driver number (102), such as 12468, Classification (104), such as dedicated driver, location (106), such as Houston Operating Center, and date of hire (108), such as Feb. 13, 2007. Other information that is not depicted but can be entered can include a box for indicating whether a driver is experienced. Personal information that a user may input include last name (110), first name (112), middle initial (114), date of birth (116), social security number (118), sex (120), height (122), and weight (124). Other information that is not depicted but can be entered can include an indication of a user's smoking history, or a history of nasal or sinus conditions, or indications of other health conditions, such as hypertension or diabetes.

FIG. 3 depicts an example sleep apnea diagnostic questionnaire requesting health information such as health conditions, personal symptoms, prior operations, and medications. Some of these questions can include: Do you have high blood pressure? (134), Do you have diabetes? (136), Have you been treated for heartburn? (138), Do you have heart problems? (140), Have you ever undergone a heart operation or procedure? (142), Do you take any of the following medications: isorbide dinitrate, such as Isordil™ or Ismo™, nitroglycerin, amiodarone, such as Cardarone™? (144), Do you have sleep apnea? (146), Do you take ANY of the following medications: metformin, such as Glucophage™, glyburide, such as Glucotrol™, Actos™, or Avandia™, or any other diabetes medications? (148), Do you have COPD (emphysema)? (150), Do you have asthma? (152), Have you been treated for depression? (154), Do you snore louder than talking? (156), Does your snoring bother other people? (158), Do you take ANY of the following medications: Plavix™, Trental™, or Persantine™? (160), Do you take ANY of the following medications: Protonix™, Prevacid™, Nexium™, Pepcid™, or Tagamet™? (162), On average, do you urinate more than once per night? (164), Do you become drowsy while driving? (166), Does head, back, neck, or joint pain affect your sleeping? (168), Do you take ANY of the following medications: enalapril, such as Vasotec™, Cozar™, Lotril™, Norvasc™, lisinopril, hydrochlorthiazide, or furosemide, such as Lasix™? (169), Do you take ANY of the following medications: Inderal™, Toprol™, Metoprolol™, Coreg™, or Lopressor™? (170), Do you take ANY of the following medications: Digoxin™, Coumadin™? (172), Do you sleep restlessly or find the blankets on the floor in the morning? (174), Has anyone noticed that you quit breathing during your sleep? (176), and Have you awakened from sleep with gasping breaths? (178). Other information that is not depicted but can be entered can include an indication of a commercial driver's smoking history, or a history of nasal or sinus conditions, or indications of other health conditions.

FIG. 4 shows an example health screening survey requesting situational answers from a situational questionnaire. The questions ask an user to input their chance of dozing while performing certain tasks. Typical tasks that are asked include: Sitting and reading (180), Watching TV (182), Sitting inactive in a public place (184), As a passenger in a car for an hour without a break (186), Lying down to rest anytime circumstances permit (188), Sitting and talking to someone (190), Sitting quietly after lunch without alcohol (192), and In a truck or car, while stopping for a few minutes in traffic (194). Figure four can also include a question requesting a male user to input his neck size (195).

FIG. 5 shows an example of a thank you screen that is shown after completing the health screening survey (196). A user would not be sent to this screen if any of the previous questions asked by the web based questionnaire was not answered. In a contemplated embodiment, the screen depicted in FIG. 5 can also include an electronic copy of a user's responses to the web based questionnaire for the user's records. It is also contemplated that an acknowledgement or verification, such as an e-mail, could also be sent and could include this information.

FIG. 6 shows an example screen of survey rankings of how an administrator would view users after they had completed the sleep apnea diagnostic screening questionnaire. Respondents are split between male and female respondents. In addition, respondents are separated into three different categories based upon the presence or absence of witnessed apneas and the presence or absence of excessive daytime sleepiness determined by each user's input information and questionnaire responses. The three categories are witnessed apnea positive(WA+) (198), witnessed apnea negative (199) and excessive daytime sleepiness positive(WA–/EDS+), and witnessed apnea negative and excessive daytime sleepiness negative(WA–/EDS–) (200). The witnessed apnea positive (198), the witnessed apnea negative and excessive daytime sleepiness positive (199), and witnessed apnea negative and excessive daytime sleepiness negative (200) categories list the number of male and female users which relate to each category. Individual users can be located as well by their social security number (206), driver number (208), and last name (210).

FIG. 7 shows an example survey rankings of how a general coordinator would be able to select commercial drivers and view their status of whether or not they had been contacted and other pertinent information. Commercial drivers would be listed with information showing their name (212), social security number (214), location (216), driver number (218), sex (220), presence or absence of witnessed apnea (225), risk rating for sleep apnea (224), whether or not they have responded positively to a question asking whether they have sleep apnea, notated as alert (226), date of entry (228), date of hire (229), and status of contacting, scheduling, and testing the commercial driver (230). The status of contacting the commercial driver (230) can include an indication that the commercial driver has been referred (231), an indication that the commercial driver has been contacted (233), an indication that the commercial driver has been scheduled for a sleep study (235), and an indication that the commercial driver has completed a sleep study (237). Additional ways that commercial drivers can be listed can include additional fields and columns tailored to the needs of a client.

FIG. 8 shows a screen of an user after an administrator had selected them and their answers to the health screening questions. Individual information of the user is shown including their name (232), social security number (234), location (236), driver number (238), sex (240), presence or absence of witnessed apnea (244), presence or absence of excessive daytime sleepiness (245), probability (246), whether or not they have been flagged for a sleep apnea follow-up (248) and a complete list of their survey responses is shown (250). FIG. 8 also includes change buttons (249), which allow a client or administrator to change or correct personal and company information, such as when a user makes a typographical error. FIG. 8 also includes a comment section (251), which allows one or more clients or administrators to enter comments regarding a specific user or specific user information, such as how a user was referred, pertinent information regarding a user's medical history, and other information. FIG. 8 is also depicted having a screening history (253) for the user. Additional individual information of the user that can be shown include an indication of smoking history, a history of nasal or sinus conditions, or other health information or information regarding medical conditions or medical history.

FIG. 9 shows the abilities of an administrator to sort and filter different users that are in the database. Different filters that an administrator can utilize include classifications (252), locations (254), and treatment facilities (256), which can be any testing facility where a sleep test is performed. An administrator can also use one or more sort menus (258), and sort by categories such as probability and status. Additional filters or sort menus that can be used include a filter or sort menu relating to administrative status, a filter relating to whether a driver is experienced, or a filter relating to date of entry or date of hire.

While these embodiments have been described with emphasis on the embodiments, it should be understood that within the scope of the appended claims, the embodiments might be practiced other than as specifically described herein.

What is claimed is:

1. A computerized system for tracking health conditions and diagnosing sleep apnea of a plurality of users associated with a client, the system comprising:
   a. a server comprising:
      (i) a data storage; and
      (ii) a processor in communication with the data storage;
   b. an encrypted web based questionnaire resident on the server, wherein the web based questionnaire comprises computer instructions for receiving input information from a user, wherein the input information comprises:
      (i) company employee information;
      (ii) personal health information that includes a prior health condition of the user, a prior operation of the user, a medication taken by the user, user self admitted sleep apnea, user reported diabetes, user reported emphysema or lung disease, user reported asthma, user reported depression, user reported snoring, user reported heart burn, user reported frequent urination at night; witnessed sleep apnea of the user, excessive daytime sleepiness of the user, and restless sleep reported by the user; and (iii) individual personal information that includes gender of the user, social security number of the user, the age of the user, the weight of the user, the height of the user, the date of birth of the user;

c. computer instructions stored on the data storage to display the encrypted web based questionnaire resident on the server and to accept input information from the encrypted web based questionnaire from the user;

d. computer instructions stored on the data storage to categorize the user into one of six categories based on the input information, wherein the categories comprise a male witnessed apnea positive category, a female witnessed apnea category positive, a males excessive daytime sleepiness positive with negative witnessed apnea category, a female excessive daytime sleepiness positive with negative witnessed apnea category, a male witnessed apnea negative and excessive daytime sleepiness negative category, and a female witnessed apnea negative and excessive daytime sleepiness negative category;

e. computer instructions stored on the data storage to perform an odds ratio calculation in combination with a linear regression model on the personal health information and the individual personal information to determine a rating that relates to the risk of sleep apnea for the user having input information in the category of males excessive daytime sleepiness positive with negative witnessed apnea;

f. computer instructions on the data storage to perform an odds ratio calculation on the personal health information and the individual personal information to determine a rating that relates to the risk of sleep apnea for the user having input information in the category of female excessive daytime sleepiness positive with negative witnessed apnea;

g. computer instructions on the data storage to perform an odds ratio calculation on the personal health information and the individual personal information to determine a rating that relates to the risk of sleep apnea for the user having input information in the category of male witnessed apnea negative and excessive daytime sleepiness negative;

h. computer instructions on the data storage to perform an odds ratio calculation on the personal health information and the individual personal information to determine a rating that relates to the risk of sleep apnea for the user having input information in the category of female witnessed apnea negative and excessive daytime sleepiness negative; and i. computer instructions stored on the data storage to allow a client to generate a list and view the status of a plurality of users, wherein the list displays each user's risk of sleep apnea, a means to contact each user, and an indication of whether the user has been scheduled for a sleep study j. wherein the odds ratio calculation in combination with a linear regression model comprises exploring models with main effects and pair-wise interactions with two or more of the following variables: body mass index, age, hypertension, diabetes, heartburn, heart conditions, snoring, asthma, depression, frequent urination at night and painful sleep.

2. The system of claim 1, wherein the user is a commercial truck driver, chemical pant employee, a bus driver, a cab driver, a boat pilot, a railroad engineer, a railroad conductor, a boat captain, a military person, a law enforcement person, a emergency response person, a medical professional, a driller, a miner, an operator of heavy machinery, or combinations thereof.

3. The system of claim 1, wherein the company employee information comprises: a name of a company, a driver number, a location, a date of hire, or combinations thereof.

4. The system of claim 1, wherein the client is a commercial carrier.

5. The system of claim 1, wherein the encrypted web based questionnaire further comprises a situational questionnaire, and wherein the situational questionnaire comprises gender related questions.

6. The system of claim 1, further comprising computer instructions stored on the data storage to generate a web based health screening service report for the plurality of users.

7. The system of claim 6, wherein the web based health screening service report comprises:

a. a rating that indicates a positive predictive value for each user of the plurality of users, wherein the rating is a numerical score; a rating of high, medium, or low; or combinations thereof;

b. a self admitted sleep apnea section, which separates a self-identified set of users from the plurality of users who indicated they had sleep apnea;

c. a body mass index section, which identifies a body mass index for each user from the plurality of users;

d. a summary of results of a sleep test section for a set of sleep study participants from the plurality of users, wherein the sleep test section displays an apnea/hypopnea index, an oxygen saturation nadir, an oxygen desaturation index, or combinations thereof for the sleep study participants;

e. a periodic limb movement section, which indicates a presence of stereotypical limb movements associated with EEG arousal during the sleep test; or f. combinations thereof.

8. The system of claim 7, wherein the web based health screening service report further comprises a search field allowing the client to locate each user of the plurality of users by name, by employee information, by social security number, or combinations thereof.

9. The system of claim 1, further comprising computer instructions on the data storage to display survey rankings on a screen to allow an administrator to view the results of the encrypted web based questionnaire for each user of the plurality of users, wherein the screen allows the administrator to locate the user by social security number, driver number, last name, or combinations thereof.

10. The system of claim 1, further comprising computer instructions on the data storage to allow an administrator to select a user from the plurality of users, and wherein the user is individually associated with a health screening survey results screen for specific to that user, and wherein the health screening survey results screen comprises:

a. change buttons to allow the administrator to change personal and company information on the health screening survey results screen; and b. a comments section that allows the administrator to enter comments regarding the user.

11. The system of claim 10, further comprising at least one filter or at least one sort menu, allowing an administrator to filter or sort the plurality of users.

12. The system of claim 11, wherein the at least one filter comprises: probability of sleep apnea, administrative status, date of hire, date of entry, or combinations thereof.

* * * * *